US010067086B2

(12) United States Patent
Genies et al.

(10) Patent No.: US 10,067,086 B2
(45) Date of Patent: Sep. 4, 2018

(54) METHOD FOR THE IN-SITU RECALIBRATION OF A COMPARISON ELECTRODE INCORPORATED INTO AN ELECTROCHEMICAL SYSTEM

(71) Applicant: RENAULT s.a.s., Boulogne-Billancourt (FR)

(72) Inventors: Sylvie Genies, Saint Egreve (FR); Melanie Alias, Poligny (FR); Sylvain Leirens, Grenoble (FR); Angel Zhivkov Kirchev, Aix les Bains (FR)

(73) Assignee: RENAULT s.a.s., Boulogne-Billancourt (FR)

( * ) Notice: Subject to any disclaimer, the term of this patent is extended or adjusted under 35 U.S.C. 154(b) by 171 days.

(21) Appl. No.: 15/038,192

(22) PCT Filed: Nov. 14, 2014

(86) PCT No.: PCT/FR2014/052908
§ 371 (c)(1),
(2) Date: May 20, 2016

(87) PCT Pub. No.: WO2015/075359
PCT Pub. Date: May 28, 2015

(65) Prior Publication Data
US 2016/0290959 A1     Oct. 6, 2016

(30) Foreign Application Priority Data

Nov. 21, 2013    (FR) ...................................... 13 61465

(51) Int. Cl.
*G01N 27/41*      (2006.01)
*H01M 10/48*     (2006.01)
(Continued)

(52) U.S. Cl.
CPC ....... *G01N 27/4163* (2013.01); *G01N 27/301* (2013.01); *H01M 10/48* (2013.01);
(Continued)

(58) Field of Classification Search
None
See application file for complete search history.

(56) References Cited

U.S. PATENT DOCUMENTS

2009/0104510 A1    4/2009   Fulop et al.
2009/0294306 A1*   12/2009   Feldman .............. G01N 27/301
                                                                          205/792

(Continued)

OTHER PUBLICATIONS

International Search Report dated Feb. 4, 2015 in PCT/FR2014/052908 Filed Nov. 14, 2014.

*Primary Examiner* — Scott J Chmielecki
(74) *Attorney, Agent, or Firm* — Oblon, McClelland, Maier & Neustadt, L.L.P.

(57) ABSTRACT

A method recalibrates in situ a comparison electrode integrated into an electrochemical system. The electrochemical system includes a working electrode, a counter electrode, and an electrolyte. The method includes verifying a potential of the comparison electrode relative to the working electrode or to the counter electrode in situ, detecting whether there is a drift in the potential of the comparison electrode relative to a potential plateau for which the comparison electrode was functionalized or designed, and when the drift is detected, recalibrating the comparison electrode in situ.

7 Claims, 5 Drawing Sheets

(51) Int. Cl.
*H01M 6/50* (2006.01)
*G01N 27/416* (2006.01)
*G01N 27/30* (2006.01)
*H01M 10/052* (2010.01)
*H01M 10/42* (2006.01)

(52) U.S. Cl.
CPC ........ *H01M 6/5005* (2013.01); *H01M 10/052* (2013.01); *H01M 2010/4271* (2013.01)

(56) References Cited

U.S. PATENT DOCUMENTS

| | | |
|---|---|---|
| 2011/0250478 A1* | 10/2011 | Timmons .............. H01M 4/485 429/91 |
| 2012/0263986 A1 | 10/2012 | Fulop et al. |
| 2013/0009604 A1 | 1/2013 | Bhardwaj et al. |
| 2014/0023888 A1 | 1/2014 | Fulop et al. |

* cited by examiner

METHOD FOR THE IN-SITU RECALIBRATION OF A COMPARISON ELECTRODE INCORPORATED INTO AN ELECTROCHEMICAL SYSTEM

The technical field of the invention is electrochemical systems, in particular what are referred to as three-electrode electrochemical systems, containing a comparison electrode.

An electrochemical system consists at least of one working electrode and one counter electrode that are submerged in an electrolyte and separated by a separator. It is possible to add a third electrode, the potential of which is stable and known, to such systems, thereby allowing the potential of each electrode to be measured independently during the redox reactions. This third electrode is considered to be a reference electrode (RFT) if its electrochemical potential, given by the Nernst equation (see Eq. 2), does not vary over time. This stability is possible if the activities of the species of the electrochemical couple $Ox_{Ref}/Red_{Ref}$ present does not vary over time.

The electrochemical reaction allowing the oxidizing species to be converted to the reducing species, and vice versa, is characterized by the following equation:

$$c\ Ox_{Ref} + n\ e^- \leftrightarrows d\ Red_{Ref} \qquad (Eq.\ 1)$$

The potential associated with this reaction is given by the following equation:

$$E = E^0 + \frac{RT}{nF}\ln\frac{a_{Ox_{Ref}}^c}{a_{Red_{Ref}}^d} \qquad (Eq.\ 2)$$

where E: Electrochemical potential (V);
E°: Standard electrochemical potential (V), i.e. measured under standard pressure and temperature conditions;
R: Ideal gas constant (8.314 J·K$^{-1}$·mol$^{-1}$);
T: Temperature (K);
n: Number of electrons (e$^-$) exchanged;
c,d: Stoichiometric coefficients of the electrochemical reaction;
F: Faraday constant (96485 C·mol$^{-1}$);
$a_{Ox_{Ref}}$: Coefficient of activity of the oxidizing species of the electrochemical couple;
$a_{Red_{Ref}}$: Coefficient of activity of the reducing species of the electrochemical couple.

The third electrode may also be a comparison electrode (CPE). In this case, its electrochemical potential is not perfectly stable. It may vary slightly over time because of the variation in one of the activities of the species of the electrochemical couple $Ox_{Ref}/Red_{Ref}$ present, thus modifying the equilibrium of the redox reaction. However, this variation is very slow. If this electrode is used for a sufficiently short length of time relative to the rate at which its potential drifts, the electrode may be considered to be a reference electrode. If its use is prolonged therebeyond, the drift in its potential must be taken into account.

Figure 1A:
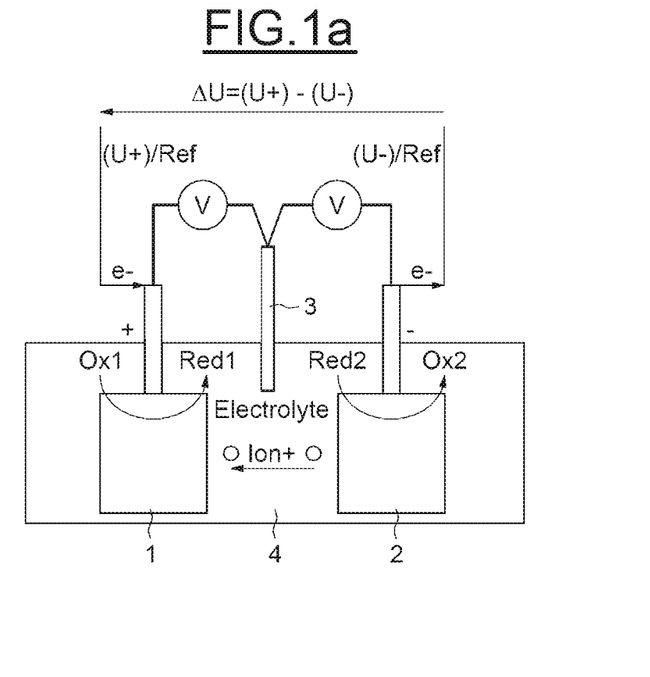
FIGS. 1a and 1b illustrate an electrochemical system comprising a comparison electrode, according to the prior art.
Figure 1B:
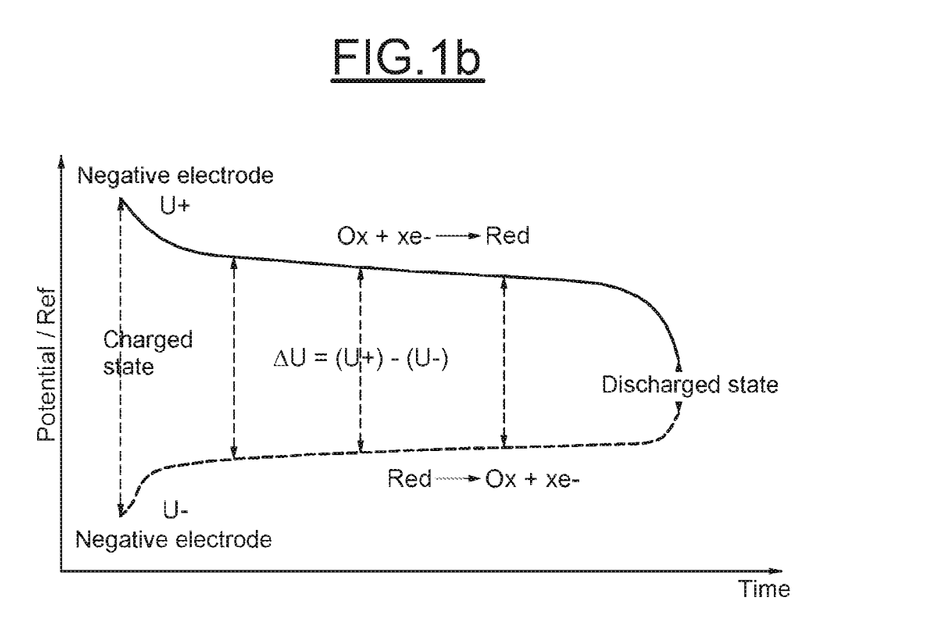

FIG. 1 illustrates an accumulator consisting of a positive electrode (working electrode) and a negative electrode (counter electrode). The integration of an RFE or a CPE into an accumulator allows the profile of the potential on each electrode during the charging and discharging processes to be characterized and their electrochemical properties to be characterized as a function of the state of charge and state of ageing of the accumulator.

These electrochemical properties may be measured by applying various currents or potentials (frequency-dependent variation, time-dependent variation). Mention may be made of internal resistance, interface resistance, charge-transfer resistance, characteristic frequencies, and diffusion coefficient. It is possible, for example, to obtain an impedance spectrum by applying a frequency-dependent voltage (or current) signal to a composite electrode. From analysis of such spectra, parameters may be calculated for particular frequencies, and their variations correlated with a state of health, in terms of power for example.

An accumulator is an electrochemical system comprising a working electrode and a counter electrode submerged in an electrolyte. FIG. 1a illustrates such a system. Certain accumulators comprise a comparison electrode. Reference will be made below to lithium-ion accumulators.

The comparison electrode is designed in order that the electrochemical couple chosen has a potential plateau over an extensive range of states of charge and is stable in the electrolyte. The reduced species the potential of which is the most reducing must be comprised in the electrochemical stability window of the electrolyte. At the present time, various redox couples are used to serve as comparison electrodes in lithium-ion type electrochemical systems:

For these materials, the Nernst equation presented above may be reformulated depending on the degree of insertion x of lithium in the comparison electrode in the following way:

$$E = E^0 + \frac{RT}{nF}\ln\frac{(1-x)}{x} \qquad (Eq.\ 3)$$

where x: degree of insertion varying in the following way: $0 < x < 1$

The concentration of one of the components may vary over time because of modification of the concentration of Li ions in the electrolyte for the Li$^+$/Li couple, or because of the variation in the degree of insertion x in the insertion structure by self-discharge. This implies that these electrodes are comparison electrodes.

At a fundamental level, the RFE allows the electrochemical effects that take place at the electrodes to be better understood. As FIG. 1b shows, the voltage measured across the terminals of the element is a simple difference in the potentials of each of the two electrodes. It is therefore a relative measure that does not represent the potential of each of the two electrodes. This electrode potential value, which could be qualified an absolute value, can only be obtained by measuring the voltage relative to a fixed potential. Such a fixed potential is given by the RFE. It is thus possible to detect the appearance of a drift in potential toward zones of overcharge or over-discharge, or indeed even to detect secondary reactions occurring on the margins of the main electrochemical reactions.

At an applied level, the RFE allows the corrosion potential of a metal to be measured and the end-of-charge or end-of-discharge potential threshold of the electrodes to be detected in complement to the voltage threshold of the electrochemical system as proposed in the prior art.

The RFE also allows an indicator of state of health to be obtained by monitoring of a representative electrical parameter such as internal resistance, surface resistance or a combination of a plurality of these parameters.

In the first case, the use of the comparison electrode is most often limited in time. As the drift in the potential may be considered to be insignificant, the term RFE is used in place of the term CPE.

In the second case, and more particularly during use of a CPE as a sensor for evaluating the state of operation of an accumulator, the CPE must deliver reliable information throughout the lifetime of the accumulator. However, this is not possible since drift in its potential corrupts the measurement.

The following documents are known from the prior art.

Document US 200910104510 A1 discloses the use of an RFE to measure states of charge and of health for lithium-ion batteries. The type of RFE proposed is a biphasic material in order to provide a stable voltage plateau whatever the lithiation state of the electrochemical couple in question of the RFE. The most preferred couple in this patent is lithium titanate $Li_4Ti_5O_{12}/Li_7Ti_5O_{12}$. A nonexhaustive list given in the patent mentions other couples, in particular lithium-containing alloys and lithium phosphates.

Document JP2010218900 protects the use of an RFE to protect the accumulator from overcharging by control of the potential of the negative electrode.

However, the electrodes, which are based on a coated material (for example made of LTO (lithium titanates) or of LFP (lithium iron phosphate) or alloys), age over time, and this ageing accelerates with temperature, this leading to a relatively rapid drift in the voltage measurement.

Because of this drift, the measurement of the potentials of the positive and negative electrodes will over time become corrupted and the setpoint extracted from these measurements will lead to the accumulator being operated in an incorrect voltage range that will cause the element to degrade (overcharge, over-discharge), and will possibly even be dangerous (overcharge).

The problem of drift in the potential of the comparison electrode arises in lithium electrochemical systems, as was explained above. However, similar drifts may be observed in electrochemical systems that do not employ lithium.

There is therefore a need for an electrochemical system and method allowing a comparison electrode exhibiting an unacceptable (excessive or too rapid) drift to be recalibrated in situ.

There is also a need for an electrochemical system and method allowing the state of health of a comparison electrode to be evaluated.

The subject of the invention is a method for recalibrating in situ a comparison electrode integrated into an electrochemical system comprising a working electrode, a counter electrode and an electrolyte. The method comprises the following steps:

the potential of the comparison electrode relative to the working electrode or to the counter electrode is verified in situ;

it is detected whether there is a drift in the potential of the comparison electrode relative to the potential plateau for which it was functionalized or designed; and if such is the case, the comparison electrode is recalibrated in situ.

It will be noted that the potential of the comparison electrode may be verified relative to a positive or negative electrode that is fully inserted or disinserted with the chemical species of the ionic element contained in the electrolyte.

The potential of the comparison electrode relative to the working electrode or to the counter electrode may be verified in situ by applying the following steps:

the potential of the comparison electrode is measured; then a verification current of positive amplitude is applied for a first duration; then a first variation in the potential of the comparison electrode is measured; then a verification current of negative amplitude is applied for a second duration; then a second variation in the potential of the comparison electrode is measured; then a voltage measurement is determined depending on the first variation and the second variation in potential.

The product of the amplitude of the verification currents multiplied by the first duration may be at least equal to one tenth of the maximum charge of the comparison electrode.

It may be determined that there exists a drift in the potential of the comparison electrode if the measured voltage is higher than the plateau voltage increased, for a given temperature, by a shift voltage value preferably at least equal to 20 mV±5 mV.

The potential of the comparison electrode may be verified and drift in the potential of the comparison electrode detected periodically, especially depending on the time period that has passed since the last functionalization.

The potential of the comparison electrode may be verified during a period of relaxation of the electrochemical system consecutive to a complete recharge.

If a drift in potential is observed, the comparison electrode may be recalibrated by carrying out the following steps:

a recalibration current of negative amplitude is applied until a first variation in potential; then the potential value obtained is memorized by way of lower bound; then a recalibration current of positive amplitude is applied, until a second variation in potential; then the potential value obtained is memorized by way of upper bound; then the capacity of the comparison electrode is next determined depending on the lower potential bound, on the upper potential bound and on the applied current; then the state of ageing of the comparison electrode is determined from its initial capacity and the determined capacity;

if the state of ageing is above a threshold, a negative current is applied in order to obtain a state of charge; and if such is not the case, the comparison electrode is declared to have failed.

The comparison electrode may be recalibrated by applying in succession a recalibration current of positive amplitude then a recalibration current of negative amplitude in order to reposition the potential of the comparison electrode on the potential plateau.

The product of the amplitude of the recalibration currents multiplied by the duration of application of the recalibration currents may be higher than one fifth of the total charge of the comparison electrode.

Other aims, features and advantages will become apparent on reading the following description, which is given merely by way of nonlimiting example and with reference to the appended drawings, in which.

FIG. 1a illustrates an electrochemical system comprising a working electrode 1, a counter electrode 2 and a comparison electrode 3 all three submerged in an electrolyte 4. The electrolyte 4 may be liquid or solid. The voltage ΔU available during discharge depends on the difference in the potentials U+ and U− on the terminals of the working electrode and counter electrode. It may also be seen that the potentials U+ and U− on the terminals of the working electrode and counter electrode are measured relative to the comparison electrode 3. FIG. 1b for its part illustrates the variation in the potentials of the working electrode and counter electrode as a function of the charged and discharged state of the accumulator, and, incidentally, of the oxidized or reduced state of these electrodes.

One embodiment of the invention relating to a method for recalibrating in situ a comparison electrode (CPE) integrated into an electrochemical system will now be described. The technology in question is more particularly the lithium-ion technology. This technology, because of the reactivity of its components with respect to moisture in the air, requires seal-tight packages to be used. The integration of a CPE takes place at the time of manufacture of the element thereby preventing subsequent replacement of the CPE. The expected lifetime of lithium-ion accumulators is about 10 to 15 years in applications that will be affected by the variation over time of the power or energy characteristics of the accumulator.

Over such a lifetime, the electrochemical potential of a CPE will gradually get further from its plateau potential and drift, as was explained above.

The drift of the potential of the comparison electrode has multiple causes, such as self-discharge, the presence of a microcurrent between the CPE and the electrodes of the electrochemical cell via the measuring instrument or calendar ageing. To limit calendar ageing, it is possible and even important to adjust the initial state of charge at the moment of the functionalization of the CPE (for example for an electrode made of LTO). Specifically, the state of charge influences ageing, which may then be greatly decreased by choosing the most suitable state of charge.

Despite these precautions and because of other influencing factors, the potential of the comparison electrode drifts over time and therefore delivers erroneous values of the potential of the positive and negative electrodes. The information delivered is then no longer exploitable.

Figure 2:
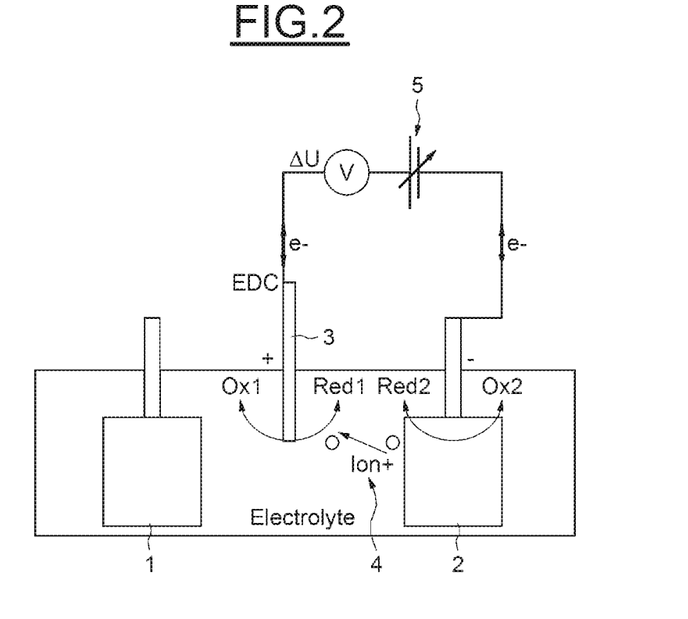
FIG. 2 illustrates the connection of the electrodes of an electrochemical system prior to a recalibration.

It is possible to correct the drift of the comparison electrode by performing a recalibration by virtue of the use of one of the two, positive or negative, electrodes of the electrochemical cell. The electrode used is preferably that with the highest capacity. The re-functionalization of the comparison electrode consumes only an infinitesimal part of the capacity of the electrode used because the active material of the comparison electrode has an infinitesimal capacity relative to the capacity of the electrodes of the electrochemical cell. An exemplary arrangement of connections before recalibration is given in FIG. 2. In this figure, it may be seen that the comparison electrode 3 and the counter electrode 2 are connected by way of a variable voltage source 5.

In other words, the method for recalibrating (or re-functionalizing) the comparison electrode allows it to be returned to a stable potential domain, thus allowing it to be requalified as an in situ reference electrode. As was mentioned above, a lithium-ion accumulator is sealed tight and, since the CPE is integrated at the time of manufacture, it is therefore not possible to carry out an ex situ recalibration without damaging the accumulator. It is therefore necessary to carry out an in situ recalibration.

A number of methods may be applied to detect drift in the potential of the comparison electrode:
  Periodic re-functionalization (as a function of time for example);
  Re-functionalization after detection of an abnormal variation in the potential of the positive and negative electrode during periods of relaxation after complete recharge;
  Re-functionalization after verification that the potential of the CPE is no longer on the voltage plateau.

Figure 3:
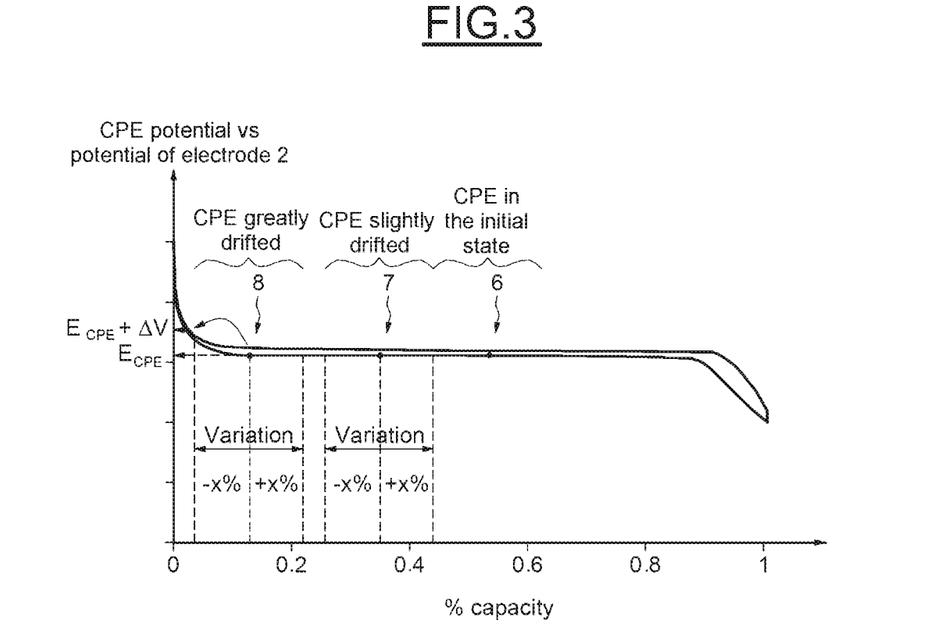
FIG. 3 illustrates the curve of the potential of the comparison electrode relative to the counter electrode 2 as a function of the capacity of the electrochemical system.

FIG. 3 illustrates the latter case. The state of charge of the CPE is represented by the point referenced 6 on the curve of the potential of the comparison electrode relative to the counter electrode 2 as a function of the capacity of the electrochemical system. As may be seen, this state of charge may vary during the discharge of the system even though the potential of the CPE remains on the potential plateau. However, depending on the state of charge of the electrochemical system, the state of charge (SOC) of the CPE may get close to the initial state, represented by the point referenced 7, or indeed to one of the ends of the plateau, represented by the point referenced 8. The CPE is considered to need to be re-functionalized when its state of charge is located at the point 8. To verify whether the CPE is in such a situation, the CPE is loaded for a time t with in succession a positive then negative current of amplitude equivalent to a regime higher than C/10 and lower than or equal to C. This load induces a small variation in its state of charge, thereby generating a variation in the potential of the comparison electrode. By measuring this variation in potential, it is possible to determine the state of the comparison electrode It will also be recalled that the state of lithiation of the comparison electrode is related to its potential by the Nernst equation described above (Eq. 3). Thus, the potential of the electrode will vary depending on whether it does not comprise inserted lithium ions (fully delithiated state) or whether it comprises the maximum amount of inserted lithium ions (fully lithiated state).

The potential of the comparison electrode therefore varies:
  without significant variation, on the voltage plateau, if the state of charge is in the zone of the plateau (Ref. 7); or
  significantly if the state of charge is at the end of the voltage plateau (Ref. 8), in the delithiated state.

The potential of the counter electrode 2 (negative electrode of the element for the presented case) may be considered to be invariant because the charge (in A.h) used during the charging and discharging cycle is very small. The charge used is not enough to make the state of charge of the electrochemical system and therefore the potentials of the various electrodes vary significantly. An observed drift in potential is thus indeed related to a drift in the potential of the comparison electrode off of the potential plateau.

It is important to determine the maximum value of the acceptable drift in potential relative to the plateau potential measured during application of a current load at a given temperature and for a length of time long enough to allow variations in charge to be smoothed out, for example 1 h. The process of re-functionalization will be triggered if the following condition is met:

$$|U\text{measured }(T,I=C/10)|>|U\text{plateau}(T,I=C/10)|+20 \text{ mV} \quad \text{(Eq.4)}$$

Where:
$U_{measured}$: Measured voltage
$U_{plateau}$: Plateau voltage
T: Temperature of the system
I: Current employed
C: Nominal capacity of the CPE Once a drift in the potential of the comparison electrode larger than the threshold value, here for example 20 mV, is observed, the re-functionalization may be carried out.

One difficulty then resides, in light of the fact that the electrode 2 is in a variable and uncontrolled state of charge at the moment of the re-functionalization procedure, in the determination of the upper and lower voltage bounds. The voltage of the CPE measured relative to the electrode 2 depends on the voltage of the electrode 2.

A number of methods may be applied.

In a first method, a negative current −I (chosen depending on the nature of the CPE for a >C/5 regime) is applied so as to lithiate the material of the comparison electrode until a variation in potential signifying that the electrode is fully lithiated is observed. This value is memorized as the lower bound (B−).

Next, a positive current +I, having an absolute value of the same amplitude as the negative current, is applied. The application of this current allows the material of the comparison electrode to be delithiated until a variation in potential signifying that the electrode is full delithiated is observed. This value is memorized as the upper bound (B+).

Next, the actual capacity of the CPE and its state of ageing relative to its initial capacity are determined. The actual capacity of the CPE is determined by integrating the current I over the time taken for the potential to vary from (B−) to (B+):

$$\text{Actual capacity} = \int_0^t I(t)dt \quad \text{(Eq. 5)}$$

If the applied current I that causes the potential to vary between (B−) and (B+) is considered to remain constant, Eq. 5 may be written:

$$\text{Actual capacity} = I \cdot t \quad \text{(Eq. 6)}$$

The initial capacity is measured following the same protocol during the first functionalization, considered to be the initial state. The state of ageing, expressed in percent, is given by:

$$\text{State of ageing} = \frac{\text{Actual capacity}}{\text{Initial capacity}} \times 100 \quad \text{(Eq. 7)}$$

Lastly, a negative current is applied in order to lithiate the CPE to the desired state of charge. The current may be applied in order to achieve a charge in A.h. The amount of electricity A.h is determined depending on the desired state of charge, on the bounds (B+) and (B−) and on the currents +I and −I.

If the current is known, the duration of application is determined in order to achieve the same charge in A.h.

In a second method, a positive then negative current variation is applied in succession to reposition the potential of the CPE on the plateau. However, this method does not allow the state of charge of the CPE to be set with precision.

Figure 4:
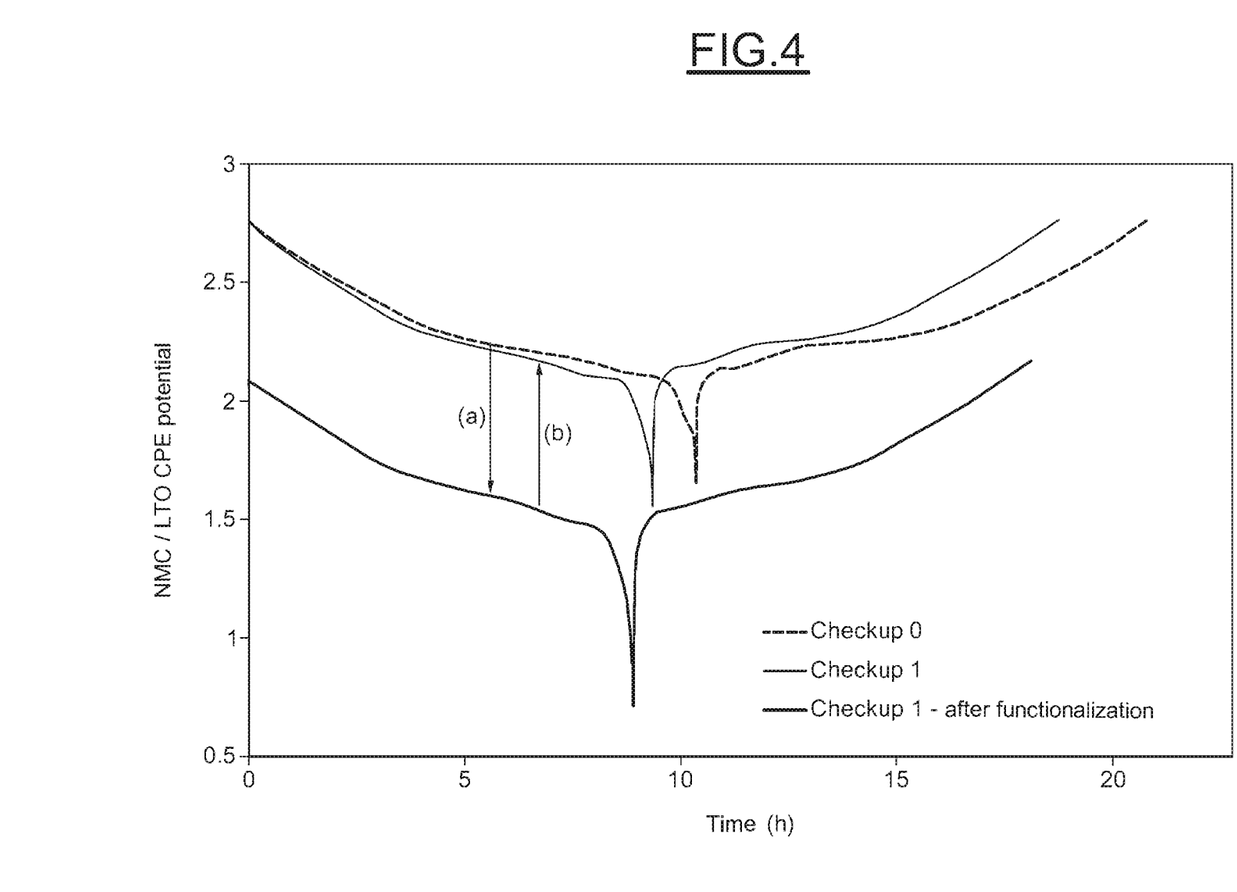
FIG. 4 illustrates profiles of the potential on a positive electrode made of lithium nickel manganese cobalt oxide $LiNi_xMn_yCo_zO_2$ (NMC) integrated into a graphite/NMC lithium-ion element and cycled at 45° C.

FIG. 4 shows profiles of the potential on a positive electrode made of lithium nickel manganese oxide $LiNi_x Mn_y Co_z O_2$ (NMC) integrated into a graphite/NMC lithium-ion element and cycled at 45° C.

FIG. 4 shows two profiles of the potential of the electrode, before cycling (Checkup 0) and after 100 cycles (Checkup 1) without functionalization. A shift in the potential of the electrode made of NMC may be observed between the Checkup 0 and the Checkup 1. This shift is not related to a degradation in the electrical properties of the electrode (increase in its internal resistance) but to a drift in the potential of the LTO CPE (or LTO RFE) used as a reference. This drift was removed by re-functionalizing the RFE by applying the first recalibrating method described above. The result of this recalibration may be seen in FIG. 4 from the potential profile (Checkup 1—after re-functionalization). This profile of the potential of the electrode made of NMC after functionalization is indeed in the same potential domain as during the Checkup 0.

Figure 5:
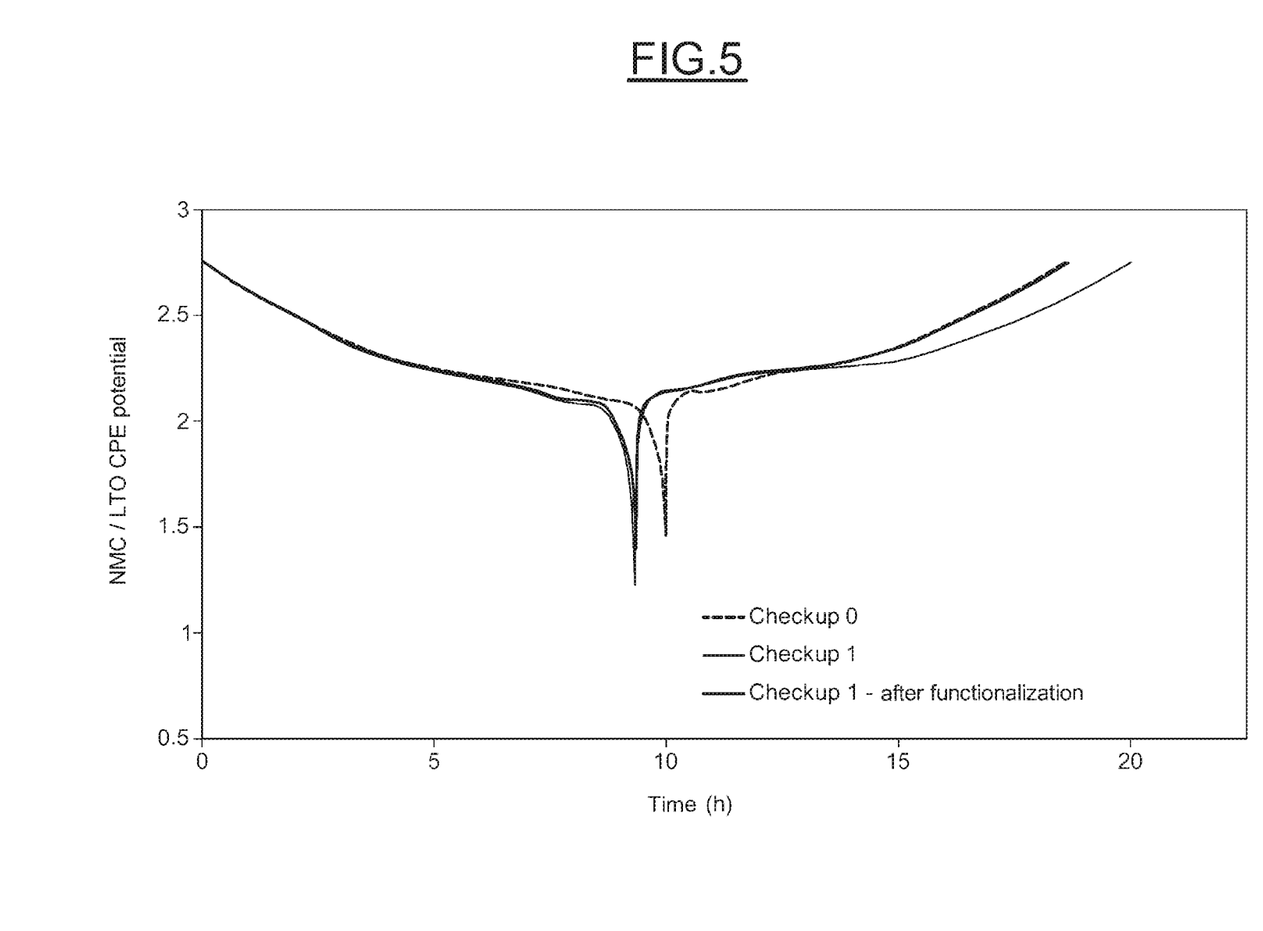
FIG. 5 illustrates profiles of the potential on a positive electrode made of lithium nickel manganese cobalt oxide $LiNi_xMn_yCo_zO_2$ (NMC) integrated into a graphite/NMC lithium-ion element and cycled at 25° C.

This drift is related to a self-discharge effect that was thermally accelerated by carrying out the element cycling test at 45° C. A similar test carried out at 25° C. is illustrated in FIG. 5. It may be seen that the drift is less substantial under such conditions, all the other test conditions moreover being equivalent.

Figure 6:
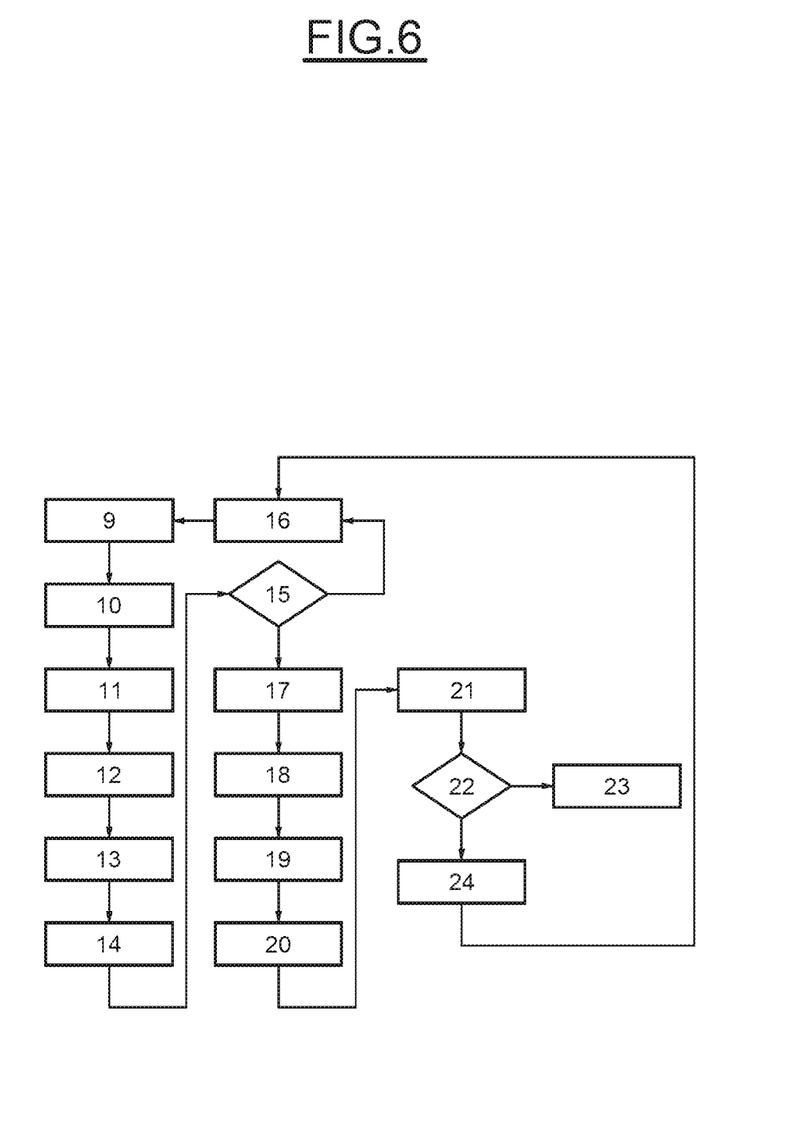
FIG. 6 illustrates the main steps of the method for recalibrating a comparison electrode in situ according to the invention.

FIG. 6 illustrates the main steps of a method for recalibrating in situ a comparison electrode.

The method comprises a step 9 in which it is determined whether the electrochemical system is in a relaxation phase, i.e. no positive current (entering) or negative current (exiting) is being applied, after a complete charge. This relaxation state is confirmed by a simple measurement of the current which must be zero.

If such is the case, the method continues in step 10, in which the connections of the electrodes are modified so that the comparison electrode is connected to the working electrode or to the counter electrode of the electrochemical system in order to make it possible for a current to flow.

In a step 11, a verification current of positive amplitude is applied for a first duration.

In a step 12, the variation in the potential of the comparison electrode relative to the other electrode to which it is connected is measured. To do this, the potential of the comparison electrode relative to the other electrode before the application of the positive current is subtracted from the same potential after the application of the positive current.

In a step 13, a verification current of negative amplitude is applied for a second duration. The second duration may be equal to the first duration.

The product of the amplitude of the verification currents multiplied by the respective durations is at least equal to one tenth of the maximum charge of the comparison electrode.

In a step 14, the variation in the potential of the comparison electrode relative to the other electrode to which it is connected is measured. To do this, the potential of the comparison electrode relative to the other electrode before the application of the negative current is subtracted from the same potential after the application of the negative current.

In a step 15, it is determined whether the absolute value of the difference between the potential of the comparison electrode relative to the other electrode before the application of a current and the same potential after the application of the current is smaller than a voltage threshold, for example starting from 20 mV±5 mV.

If such is the case, the method ends in a step 16 in which the working electrode, the comparison electrode and the counter electrode are reconnected so that the electrochemical system can be charged and discharged.

If such is not the case, the method continues with a step 17 in which a recalibration current of negative amplitude is applied until a potential variation larger than a first negative threshold (in mV/min) is detected.

In a step 18, the potential obtained is then memorized by way of lower voltage bound.

In a step 19, a recalibration current of positive amplitude is applied until a potential variation larger than a second positive threshold (in mV/min) is detected.

In a step 20, the potential obtained is then memorized by way of upper voltage bound.

The product of the amplitude of the recalibration currents multiplied by the duration of application of the recalibration currents is higher than one fifth of the total charge of the comparison electrode.

In a step 21, the capacity of the comparison electrode is determined depending on the lower potential bound, on the upper potential bound and on the applied current and then the state of ageing of the comparison electrode is determined from its initial capacity and the determined capacity.

In a step 22, it is determined whether the state of ageing is above a threshold. If such is the case, the method ends in the step 23 in which the comparison electrode is declared to be inoperational.

If such is not the case, the method continues with step 23, in which a negative current is applied until the desired state-of-charge value is obtained for the comparison electrode. The method then ends with the step 16 described above.

The method for recalibrating in situ a comparison electrode thus allows the initial potential of the comparison electrode to be restored in order to restore the reliability of the electrochemical system, above all in sealed systems from which it is not possible to extract the comparison electrode. The method thus allows the lifetime of such systems to be prolonged and electrochemical systems the comparison electrode of which has failed to be determined.

The invention claimed is:

1. A method for recalibrating in situ a comparison electrode integrated into an electrochemical system including a working electrode, a counter electrode, and an electrolyte, the method comprising:
   connecting the comparison electrode to the working electrode or the counter electrode;
   verifying a potential of the comparison electrode relative to the working electrode or to the counter electrode in situ by
      measuring the potential of the comparison electrode, then
      applying a verification positive current of a first duration, then
      measuring a first variation in the potential of the comparison electrode, then
      applying a verification negative current of a second duration, then
      measuring a second variation in the potential of the comparison electrode, and then
      determining a voltage measurement depending on the first variation in the potential and the second variation in the potential;
   detecting whether there is a drift in the potential of the comparison electrode relative to a potential plateau for which the comparison electrode was functionalized or designed when either the first variation in the potential of the comparison electrode or the second variation in the potential of the comparison electrode is greater than a plateau voltage for which the comparison electrode was functionalized or designed increased, for a given temperature, by a shift voltage value; and
   when the drift is not detected, reconnecting the comparison electrode to the working electrode or the counter electrode so that the electrochemical system can be charged and discharged,
   when the drift is detected, recalibrating the comparison electrode in situ by
      applying a recalibration negative current until the first variation in the potential, then
      memorizing a potential value obtained by lower bound, then
      applying a recalibration positive current until the second variation in the potential, then
      memorizing the potential value obtained by upper bound, then
      determining a capacity of the comparison electrode depending on the lower bound, the upper bound, and applied currents, and then
      determining a state of ageing of the comparison electrode from an initial capacity and the determined capacity, and
   when the state of ageing is not above a threshold, applying the negative current to obtain a state of charge, and reconnecting the comparison electrode to the working electrode or the counter electrode so that the electrochemical system can be charge and discharged, and
   when the state of ageing is above a threshold, determining that the comparison electrode has failed.

2. The method as claimed in, claim 1, wherein the shift voltage value is at least equal to 20 mV±5 mV.

3. The method as claimed in claim 1, wherein the potential of the comparison electrode is verified and drift in the potential of the comparison electrode detected periodically, depending on a time period that has passed since a last functionalization.

4. The method as claimed in claim 1, wherein the potential of the comparison electrode is verified during a time period consecutive to a complete recharge, no current circulating through the electrochemical system during said time period.

5. The method as claimed in claim 1, wherein a product of an amplitude of recalibration currents multiplied by a duration of application of recalibration currents is higher than one fifth of a total charge of the comparison electrode.

6. The method as claimed in claim 1, further comprising:
   limiting intensities of the verification positive current and the first duration so that the product of an amplitude of the verification positive current multiplied by the first duration is between one tenth of the maximum charge of the comparison electrode and the maximum charge of the comparison electrode.

7. The method as claimed in claim 1, further comprising:
   limiting intensities of the verification negative current and the second duration so that the product of an amplitude of the verification negative current multiplied by the second duration is between one tenth of the maximum charge of the comparison electrode and the maximum charge of the comparison electrode.

* * * * *